(12) United States Patent
Moscoso et al.

(10) Patent No.: US 8,916,129 B2
(45) Date of Patent: Dec. 23, 2014

(54) UZM-43 AN EUO-NES-NON ZEOLITE

(71) Applicant: UOP LLC, Des Plaines, IL (US)

(72) Inventors: Jaime G. Moscoso, Mount Prospect, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 238 days.

(21) Appl. No.: 13/718,011

(22) Filed: Dec. 18, 2012

(65) Prior Publication Data

US 2014/0171291 A1   Jun. 19, 2014

(51) Int. Cl.

| | | |
|---|---|---|
| *C01B 39/48* | (2006.01) | |
| *B01J 29/70* | (2006.01) | |
| *C10G 47/16* | (2006.01) | |
| *C01B 39/12* | (2006.01) | |
| *C10G 11/05* | (2006.01) | |
| *B01J 29/88* | (2006.01) | |
| *C07C 5/22* | (2006.01) | |
| *C10G 35/095* | (2006.01) | |
| *B01J 29/064* | (2006.01) | |
| *C10G 73/38* | (2006.01) | |

(52) U.S. Cl.
CPC .............. *B01J 29/70* (2013.01); *C10G 47/16* (2013.01); *C07G 2/66* (2013.01); *C01B 39/12* (2013.01); *C10G 11/05* (2013.01); *B01J 29/88* (2013.01); *C07C 5/22* (2013.01); *C10G 35/095* (2013.01); *B01J 29/064* (2013.01); *C01B 39/48* (2013.01); *C10G 73/38* (2013.01)
USPC ........... 423/703; 423/705; 423/706; 423/707; 423/718

(58) Field of Classification Search
CPC .......... B01J 29/064; B01J 29/70; B01J 29/88; C01B 39/12; C01B 39/48; C10G 7/38; C10G 47/16; C10G 35/095; C10G 11/053; C07C 5/22; C07C 2/66
USPC ............................ 423/703, 75, 706, 707, 718
See application file for complete search history.

(56) References Cited

U.S. PATENT DOCUMENTS

| | | | |
|---|---|---|---|
| 4,057,683 A | 11/1977 | Elting | |
| 5,910,299 A * | 6/1999 | Carluccio et al. | 423/706 |
| 6,123,914 A | 9/2000 | Vaughan et al. | |
| 6,156,290 A * | 12/2000 | Lee et al. | 423/706 |
| 6,187,981 B1 | 2/2001 | Marinangeli et al. | |

(Continued)

FOREIGN PATENT DOCUMENTS

| | | |
|---|---|---|
| RU | 2340552 C2 | 12/2008 |
| RU | 2340555 C2 | 12/2008 |
| WO | WO 2010086735 A1 * | 8/2010 |

OTHER PUBLICATIONS

Search Report dated Apr. 17, 2014 for corresponding PCT Appl. No. PCT/US2013/072715.

(Continued)

*Primary Examiner* — David M Brunsman
(74) *Attorney, Agent, or Firm* — Mark Goldberg

(57) ABSTRACT

A new family of crystalline aluminosilicate zeolites has been synthesized that has been designated UZM-43. These zeolites are similar to previously known ERS-10, SSZ-47 and RUB-35 zeolites but are characterized by unique x-ray diffraction patterns and compositions and have catalytic properties for carrying out various hydrocarbon conversion processes. Catalysts made from these zeolites are useful in hydrocarbon conversion reactions.

19 Claims, 1 Drawing Sheet

(a)

(b)

(56) References Cited

U.S. PATENT DOCUMENTS

| | | |
|---|---|---|
| 6,348,183 B2 * | 2/2002 | Lee et al. ............... 423/706 |
| 6,713,041 B1 | 3/2004 | Moscoso et al. |
| 6,752,980 B1 | 6/2004 | Moscoso et al. |
| 6,890,511 B2 | 5/2005 | Rohde et al. |
| 7,063,828 B2 * | 6/2006 | Burton et al. ............. 423/706 |
| 7,454,073 B2 * | 11/2008 | Chen et al. ............... 382/239 |
| 7,459,073 B2 * | 12/2008 | Burton et al. ........... 208/111.01 |
| 8,158,103 B2 | 4/2012 | Moscoso et al. |
| 8,158,105 B2 | 4/2012 | Moscoso et al. |
| 2001/0027935 A1 * | 10/2001 | Lee et al. ................. 208/46 |
| 2004/0127762 A1 * | 7/2004 | Dalloro et al. ............ 585/475 |
| 2005/0133413 A1 | 6/2005 | Burton, Jr. et al. |
| 2005/0135998 A1 * | 6/2005 | Burton et al. ............. 423/705 |
| 2008/0216650 A1 * | 9/2008 | Falconer et al. ............ 95/51 |
| 2011/0163006 A1 * | 7/2011 | Bellussi et al. .......... 208/120.01 |

OTHER PUBLICATIONS

Marler, "Synthesis and structure of RUB-35, a disordered material of the EUO-NES-NON family", Microporous and Mesoporous Materials 64 (2003) 185-201.

Treacy, "Intergrowth Segregation in FAU-EMT Zeolite Materials", Proc. R. Soc. Lond. A (1996) 452, 813-840.

Zanardi, "Synthesis and framework topology of the new disordered ERS-10 zeolite", J Porous Mater (2007) 14:315-323.

Zanardi, "Framework Topology of ERS-10 Zeolite", Angew. Chem. Int. Ed. 2002, 41, No. 21, pp. 4109-4112.

* cited by examiner

UZM-43 AN EUO-NES-NON ZEOLITE

BACKGROUND OF THE INVENTION

The present invention relates to zeolite UZM-43, the process of making it and its use as a catalyst in hydrocarbon conversion processes. This zeolite is represented by the empirical formula:

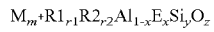

where M represents sodium or a combination of sodium and potassium exchangeable cations, "m" is the mole ratio of M to (Al+E) and varies from about 0.05 to about 5, R1 is a singly charged propyltrimethylammonium cation, "r1" is the mole ratio of R to (Al+E) and has a value of about 0.25 to about 8.0, R2 is an amine, "r2" is the mole ratio of R to (Al+E) and has a value of about 0.0 to about 5, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation: $z=(m+r1+r2+3+4 \cdot y)/2$. The zeolite UZM-43 has an intergrowth of framework EUO-NES-NON. It may be present in the catalyst as unmodified zeolite UZM-43 or as UZM-43 modified zeolite. The UZM-43 containing catalyst may take one of several forms, including for example, a spherical oil-dropped catalyst or an extruded catalyst.

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

The three structure types EUO, NON and NES are closely related and can be constructed from the same two layer building units, LBU A and LBU B, shown below extending in the a' and b' axis directions. LBU A consists of $TO_4$-tetrahedra connected in two dimensions to generate a silicate sheet with 12-ring openings. LBU B consists of linear chains of $TO_4$-tetrahedra. To generate the 3-dimensional framework structures for EUO, NON and NES, the two layer types are stacked in characteristic sequences in the c' axis direction.

Diagrams above show the layer-like building units of the EUO-NES-NON family as seen normal to (0 0 1). (a) Layer A consists of [TO4]-tetrahedra interconnected to form 12-rings and (b) layer B consists of rods of [TO4]-tetrahedra running parallel to a'

The above diagrams show representations of the framework structures and stacking sequences for (a) NON, (b) EUO and (c) NES as seen normal to (1 0 0).

For NON, only LBU A layers are stacked a). The stacking sequence is AA'AA' where every other A layer is shifted by ½a' and is designated as A'. Although the individual layers contain 12-rings, the alternating shift of ½a' blocks access and the resulting NON framework is a dense phase. It is not really a zeolite, but a clathrasil, since it contains cages (designated nns by J. V. Smith1) accessible by pores no larger than 6-rings.

The EUO framework type can be formed b) by inserting a B layer between AA' double layers giving a stacking sequence AA'BAA'B The resulting framework contains one-dimensional 10-ring channels with side pockets into truncated nns cages.

The NES framework type can be formed c) by alternating A and B layers to give a stacking sequence AB'A'BAB'A'B where A' and B' are shifted by ½a'. The resulting framework contains 2-dimensional 10-ring channels normal to the b' axis.

Several related molecular sieves have been disclosed but there are significant differences between those molecular sieves and those of the present invention. In U.S. Pat. No. 6,123,914 is disclosed an EU-1 and intergrowths of EUO-NES type of molecular sieve that is used to remove amorphous B and aluminum from the channels by using a mild treatment with sodium hydroxide. The present invention involves a silica/alumina material that does not contain boron.

U.S. Pat. No. 7,459,073 discloses a molecular sieve SSZ-47B that is made using templates that have rings and are rigid (N-cyclopentyl-1,4-diaabicyclo[2.2.2]octane cation) that would be more expensive to produce and would produce a zeolite with more EUO character than other materials.

U.S. Pat. No. 5,910,299 discloses a ERS-10 zeolite that is made using a template like 6-azonia spiro-[5,5]-undecane hydroxide. It is claimed to have a $Si/Al_2$ ratio from 50 to pure silica. The present invention is made at lower $Si/Al_2$ ratios than ERS-10.

A new material has been made comprising of an EUO-NES-NON framework intergrowth that has application in hydrocarbon processes.

SUMMARY OF THE INVENTION

As stated, the present invention relates to a new aluminosilicate zeolite designated UZM-43 that comprises an EUO-NES-NON framework intergrowth. Accordingly, one embodiment of the invention is a microporous crystalline zeolite having a three-dimensional framework of at least $AlO_2$ and $SiO_2$ tetrahedral units and an empirical composition in the as synthesized and anhydrous basis expressed by an empirical formula of:

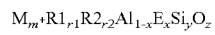

where M represents sodium or a combination of sodium and potassium exchangeable cations, "m" is the mole ratio of M to (Al+E) and varies from about 0.05 to about 5, R1 is a singly charged propyltrimethylammonium cation, "r1" is the mole ratio of R to (Al+E) and has a value of about 0.25 to about 8.0, R2 is an amine, "r2" is the mole ratio of R to (Al+E) and has a value of about 0.0 to about 5, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation:

$$z=(m+r1+r2+3+4 \cdot y)/2$$

and is characterized in that it has the x-ray diffraction pattern having at least the d-spacing's and intensities set forth in Table A.

TABLE A

| 2θ | d(Å) | I/I₀ % |
|---|---|---|
| 7.96-8.06 | 10.96-11.09 | m |
| 8.72-8.85 | 9.97-10.10 | w |
| 9.40-9.41 | 9.36-9.40 | w |
| 12.96-13.01 | 6.79-6.82 | w |
| 19.10-19.17 | 4.62-4.64 | m |
| 20.54-20.62 | 4.30-4.32 | vs |
| 22.23-22.33 | 3.97-3.99 | m |
| 23.29-23.42 | 3.79-3.81 | m-w |
| 23.97-24.08 | 3.69-3.70 | m |
| 26.01-26.13 | 3.40-3.42 | w |
| 26.54-26.62 | 3.34-3.35 | m |
| 27.24-27.32 | 3.26-3.27 | m |
| 28.86-29.00 | 3.07-3.09 | w |
| 33.16-33.29 | 2.68-2.69 | w |
| 35.46-35.52 | 2.52 | w |

After being calcined, the x-ray diffraction pattern shown in Table B was observed.

TABLE B

| 2θ | d(Å) | I/I₀ % |
|---|---|---|
| 7.99-8.00 | 11.04 | s |
| 8.74 | 10.11 | w |
| 9.42 | 9.38 | m |
| 12.96-12.99 | 6.80-6.82 | w |
| 15.24-15.27 | 5.79-5.80 | w |
| 15.98 | 5.54 | w |
| 19.22-19.26 | 4.60-4.61 | m |
| 20.56-20.62 | 4.30-4.31 | vs |
| 22.28-22.32 | 3.97-3.98 | s |
| 23.30 | 3.81 | m |
| 23.98-24.00 | 3.69-3.70 | m |
| 26.05-26.06 | 3.41 | w |
| 26.67-26.72 | 3.33 | m |
| 27.30-27.35 | 3.25-3.26 | s |
| 28.94-29.01 | 3.07-3.08 | w |
| 33.24-33.29 | 2.68-2.69 | w |
| 35.66-35.68 | 2.51 | w |

Another aspect of the invention is the process of making the material by use of propyltrimethylammonium cation (SACHEM) or propyltrimethylammonium cation and an amine. Prior art SSZ-47 materials are made by using N,N-Dimethyl-3-azoniabicyclo[4.2.1]nonane cation or N,N-Dimethyl-3-azoniabicyclo[3.2.1]octane cation which are much more expensive and produce a material that has more EUO character than the materials produced by the present invention. ERS-10 is made with another expensive template 6-azonia spiro-[5,5]-undecane hydroxide and makes a zeolite material that a higher Si/Al₂ ratio than UZM-43.

Yet another embodiment of the invention is a hydrocarbon conversion process using the above-described zeolite. The process comprises contacting the hydrocarbon with the zeolite at conversion conditions to give a converted hydrocarbon product. The hydrocarbon conversion processes include paraffin cracking, aromatic conversions such as xylene isomerization, toluene disproportionation, ring opening and cracking to remove benzene co-boilers and alkylation of aromatics with paraffins.

DETAILED DESCRIPTION OF THE INVENTION

Figure 1:
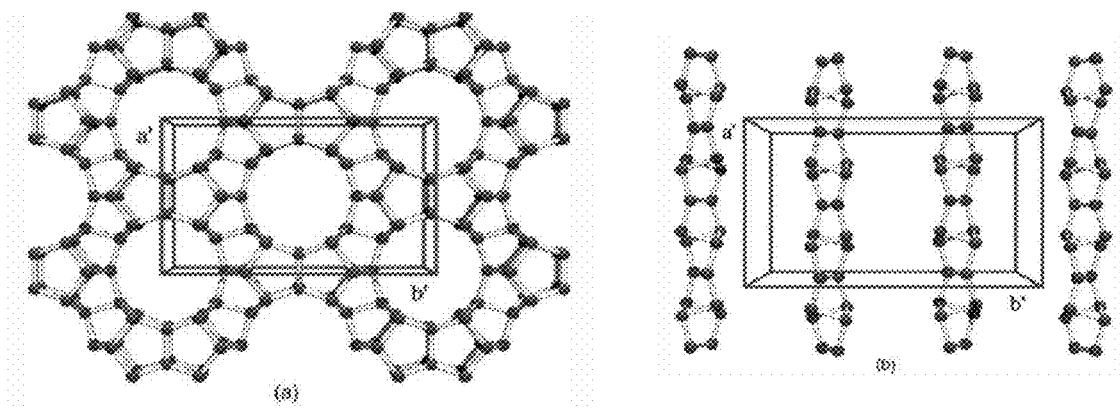
FIG. 1 shows layer-like building units of EUO-NES NON family structures.
Figure 2:
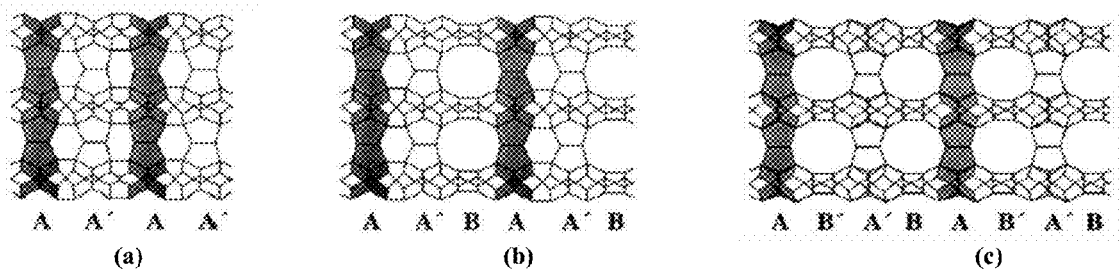
FIG. 2 shows representations of the framework structures and stacking sequences for (a) NON, (b) EUO and (c) NES as seen normal to (1 0 0).

Applicants have prepared an aluminosilicate zeolite whose topological structure fits within an EUO-NES-NON framework and are similar to RUB-35, SSZ-47 and ERS-10 types of zeolites as described in ATLAS OF ZEOLITE FRAMEWORK TYPES, which is maintained by the International Zeolite Association Structure Commission at http://topaz.ethz.ch/IZA-SC/StdAtlas.htm. These new zeolites have been designated as UZM-43. As will be shown in detail, UZM-43 is different from the known zeolites in a number of its characteristics.

As will be shown in detail in the examples, the UZM-43 material is thermally stable up to a temperature of at least 600° C. and in another embodiment, up to at least 800° C. Also as shown in the examples, the UZM-43 material may have a micropore volume as a percentage of total pore volume of greater than 60%.

The UZM material is made from a reaction mixture having a composition expressed in terms of mole ratios of the oxides of:

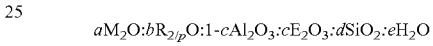

$$aM_2O:bR_{2/p}O:1-cAl_2O_3:cE_2O_3:dSiO_2:eH_2O$$

where "a" has a value of about 0.05 to about 5.0, "b" has a value of about 1.5 to about 40, "c" has a value of 0 to about 1.0, "d" has a value of about 4 to about 40, "e" has a value of about 25 to about 4000. The source of M is selected from the group consisting of halide salts, nitrate salts, acetate salts, hydroxides, sulfate salts and mixtures thereof.

The source of E is selected from the group consisting of alkali borates, boric acid, precipitated gallium oxyhydroxide, gallium sulfate, ferric sulfate, ferric chloride and mixtures thereof. The aluminum source is selected from the group consisting of aluminum isopropoxide, aluminum sec-butoxide, precipitated alumina, Al(OH)₃, aluminum metal and aluminum salts. The silicon source is selected from the group consisting of tetraethyorthosilicate, fumed silica, colloidal silica and precipitated silica. The reaction mixture is reacted at a temperature of about 150° to about 185° C. for a time of about 1 day to about 3 weeks. Preferably, the reaction mixture is reacted at a temperature of about 165° to about 175° C. for a time of about 1 day to about 3 weeks. R1 is a singly charged propyltrimethylammonium cation, "r1" is the mole ratio of R to (Al+E) and has a value of about 0.25 to about 8.0, and R2 is an amine, r2 is morpholines. The process may further comprise adding UZM-43 seeds to the reaction mixture.

EXAMPLE 1

An aluminosilicate reaction gel was prepared by first mixing 48.92 g of liquid sodium aluminate (LSA) (46.55% solution), 225.23 g of propyltrimethylammonium hydroxide (20% SACHEM), 36.11 g of morpholine (Aldrich) and 865.38 g of water while stirring vigorously. After thorough mixing, 224.36 g of Ultrasil VN SP 89% was added. After the addition was completed, the resulting reaction mixture was homogenized for 1 hour, transferred to a 2-L Parr stainless steel stir autoclave. The mixture was crystallized at 175° C. with stirring at 250 RPM for 160 hours. The solid product was recovered by centrifugation, washed with de-ionized water and dried at 95° C. The product was identified as UZM-43 by XRD. Representative diffraction lines observed for the product are shown in Table 1. The product composition was determined by elemental analysis to consist of the following mole ratios: Si/Al=13.76, Na/Al=0.23. A portion of the material was calcined by ramping to 600° C. for 2 hours followed by a 6 hour dwell in air. The BET surface area 176 m²/g and the micropore volume was 0.07 cc/g. Scanning Electron Microscopy (SEM) revealed crystals of round (grape-like) shape less than 100 nm. Chemical analysis was as follows: 3.06% Al, 42.9% Si, 0.99% Na, N/Al=0.78, Na/Al=0.38, Si/Al$_2$=27. The diffraction lines that were observed for UZM-43 are as follows in Table 1.

TABLE 1

| 2θ | d(Å) | I/I$_0$% |
|---|---|---|
| 8.02 | 11.01 | m |
| 8.72 | 10.13 | w |
| 9.4 | 9.4 | m |
| 13.01 | 6.79 | w |
| 19.17 | 4.62 | m |
| 20.62 | 4.3 | vs |
| 22.29 | 3.98 | m |
| 23.38 | 3.8 | w |
| 23.58 | 3.76 | w |
| 24.00 | 3.7 | m |
| 24.53 | 3.62 | w |
| 26.10 | 3.41 | w |
| 26.60 | 3.34 | m |
| 27.32 | 3.26 | m |
| 29.00 | 3.07 | w |
| 33.29 | 2.68 | w |
| 35.52 | 2.52 | w |

Representative diffractions lines observed for the calcined UZM-43 are shown in Table 2.

TABLE 2

| 2θ | d(Å) | I/I$_0$% |
|---|---|---|
| 7.99 | 11.04 | s |
| 9.42 | 9.38 | m |
| 12.99 | 6.80 | w |
| 14.77 | 5.98 | w |
| 15.27 | 5.79 | w |
| 15.98 | 5.54 | w |
| 19.22 | 4.61 | s |
| 20.62 | 4.30 | vs |
| 22.32 | 3.97 | s |
| 23.98 | 3.70 | m |
| 26.06 | 3.41 | m |
| 26.72 | 3.33 | m |
| 27.30 | 3.26 | s |
| 28.48 | 3.13 | w |
| 29.01 | 3.07 | w |
| 33.24 | 2.69 | w |
| 35.66 | 2.51 | w |

EXAMPLE 2

An aluminosilicate reaction gel was prepared by first mixing 48.92 g of liquid sodium aluminate (LSA) (46.55% solution), 225.23 g of propyltrimethylammonium hydroxide (20% SACHEM), 36.11 g of morpholine (Aldrich) and 865.38 g of water while stirring vigorously. After thorough mixing, 224.36 g of Ultrasil VN SP 89% was added. After the addition was completed, the resulting reaction mixture was homogenized for 1 hour, transferred to a 2-L Parr stainless steel stir autoclave. The mixture was crystallized at 175° C. with stirring at 350 RPM for 160 hours. The solid product was recovered by centrifugation, washed with de-ionized water and dried at 95° C. The product was identified as UZM-43 by XRD. Representative diffraction lines observed for the product are shown in Table 3. The product composition was determined by elemental analysis to consist of the following mole ratios: Si/Al=13.5, Na/Al=0.38 and N/Al=0.78. A portion of the material was calcined by ramping to 600° C. for 2 hours followed by a 6 hour dwell in air. The BET surface area 192 m²/g and the micropore volume was 0.07 cc/g. Scanning Electron Microscopy (SEM) revealed crystals of round shape less than 100 nm.

TABLE 3

| 2θ | d(Å) | I/I$_0$% |
|---|---|---|
| 7.96 | 11.09 | m |
| 8.72 | 10.10 | w |
| 9.41 | 9.36 | w |
| 12.96 | 6.82 | w |
| 19.10 | 4.64 | m |
| 20.54 | 4.32 | vs |
| 22.23 | 3.99 | m |
| 23.29 | 3.81 | w |
| 23.97 | 3.70 | m |
| 26.01 | 3.42 | w |
| 26.54 | 3.35 | m |
| 27.24 | 3.27 | m |
| 28.86 | 3.09 | w |
| 33.16 | 2.69 | w |
| 35.49 | 2.52 | w |

EXAMPLE 3

An aluminosilicate reaction gel was prepared by first mixing 36.61 g of liquid sodium aluminate (LSA) (46.55% solution), 24.3 g of sodium hydroxide (50% solution) and 749.05 g of water while stirring vigorously. After thorough mixing, 421.53 g of propyltrimethylammonium bromide (25% SACHEM) was added, and then 167.99 g of Ultrasil VN SP 89% was added. After the addition was completed, the resulting reaction mixture was homogenized for 1 hour, transferred to a 2-L Parr stainless steel stir autoclave. The mixture was crystallized at 175° C. with stirring at 350 RPM for 132 hours. The solid product was recovered by centrifugation, washed with de-ionized water and dried at 95° C. The product was identified as UZM-43 by XRD. Representative diffraction lines observed for the product are shown in Table 4. The product composition was determined by elemental analysis to consist of the following mole ratios: Si/Al=13.05, Na/Al=0.34. A portion of the material was calcined by ramping to 600° C. for 2 hours followed by a 6 hour dwell in air. The BET surface area 292 m²/g and the micropore volume was 0.101 cc/g. Scanning Electron Microscopy (SEM) revealed crystals of round shape less than 100 nm.

TABLE 4

| 2θ | d(Å) | I/I$_0$% |
|---|---|---|
| 8.06 | 10.96 | m |
| 8.85 | 9.97 | w |
| 12.98 | 6.81 | w |
| 19.16 | 4.62 | m |
| 20.62 | 4.30 | vs |
| 22.33 | 3.97 | s |
| 23.42 | 3.79 | m |
| 24.08 | 3.69 | m |
| 26.13 | 3.40 | m |
| 26.62 | 3.34 | m |
| 27.28 | 3.26 | s |
| 28.41 | 3.13 | w |
| 28.98 | 3.07 | w |
| 30.35 | 2.94 | w |
| 35.46 | 2.52 | w |

Representative diffractions lines observed for the calcined UZM-43 are shown in Table 5.

TABLE 5

| 2θ | d(Å) | I/I$_0$ % |
|---|---|---|
| 8.00 | 11.04 | s |
| 8.74 | 10.11 | w |
| 12.96 | 6.82 | w |
| 15.24 | 5.80 | w |
| 19.26 | 4.60 | m |
| 20.56 | 4.31 | vs |
| 22.28 | 3.98 | s |
| 23.30 | 3.81 | m |
| 24.00 | 3.70 | m |
| 26.05 | 3.41 | m |
| 26.67 | 3.33 | m |
| 27.35 | 3.25 | s |
| 28.45 | 3.13 | w |
| 28.94 | 3.08 | w |
| 30.20 | 2.95 | w |
| 33.29 | 2.68 | w |
| 35.68 | 2.51 | w |

UZM-43 synthesized as per Examples 1 and 2 were formulated into a catalyst containing 70% UZM-43 and 30% alumina. In the catalyst preparation Catapal B alumina was first peptized with nitric acid using 0.17 g of HNO$_3$ per gram of Catapal B alumina. The peptized alumina was then added to the muller, while mixing, until the dough with a proper texture for extrusion was formed. The dough was then extruded to form 1/16″ diameter cylinders, which were dried at 100° C. overnight and then sized to a length to diameter ratio of approximately 3. The dry extrudates were calcined in a box oven with a flowing air at 600° C.×5 hours to remove the template. The calcined support was then exchanged using a 10 wt-% NH$_4$NO$_3$ solution at 75° C. for 1 hour. This was followed by water wash using 10 g of water per g of zeolite. The NH$_4$NO$_3$ exchange and water wash was repeated two more times. The extrudate was then dried at 120° C. for 4 hours and then activated at 550° C.

For each of the samples listed in Table 1, comparison was made of the observed diffraction pattern with DIFFaX simulated patterns to give estimates of the αN and αS transition probabilities, which indicate EUO, NES, and NON clustering tendencies. Percentages of EUO, NES, and NON were calculated from the transition probabilities. Best fits to the simulations are summarized in Table 6.

TABLE 6

Results from DIFFaX simulations of experimental patterns

| Sample | Clustering Tendency ||| Weight Percent |||
|---|---|---|---|---|---|---|
|  | EUO | NES | NON | EUO | NES | NON |
| Sample 1 | 0.67 | 0.58 | 0.75 | 34 | 31 | 34 |
| Sample 2 | 0.67 | 0.58 | 0.75 | 34 | 31 | 34 |
| Sample 3 | 0.73 | 0.53 | 0.80 | 33 | 24 | 43 |
| SSZ-47 | 0.40 | 0.70 | 0.90 | 18 | 28 | 54 |
| RUB-35 | 1.60 | 0.10 | 0.30 | 82 | 6 | 12 |
| ERS-10 | 0.75 | 0.50 | 0.75 | 38 | 25 | 38 |

Samples 1 and 2: The synthesized samples 1 and 2 have very similar diffraction patterns and can be matched to the same DIFFaX simulated patterns. They both show only a slight tendency to cluster in NES-like regions and slightly more tendency to cluster in EUO- and NON-like regions leading to structures with slightly more EUO and NON than NES character.

Sample 3: Synthesized sample 3 has a slightly different diffraction pattern than the first two. The pattern can be fit with a simulated pattern that indicates the sample contains a little more NON character and less EUO character than the first two samples.

Regarding the diffraction of the prior art samples, the following observations were made.

ERS-10. Of the literature samples, ERS-10 has a diffraction pattern most similar to the present invention, although there are distinct differences. The pattern can be fit with a simulation indicating a similar composition, but with slightly more EUO content and Si/Al$_2$ ratio is higher than UZM-43.

The diffraction pattern for SSZ-47 is different from those for Samples 1, 2 and 3 and is consistent with a structure containing more NON character.

RUB-35 has a diffraction pattern most different from those for the samples illustrating the present invention. Its pattern is consistent with a structure with high EUO character. A model for the faulting in RUB-35 was developed which did not consider clustering. Their best fit was to a structure with 78% EUO-type and 22% NON-type character. The model reported here gives a similar result (82% EUO, 12% NON, 8% NES) but also indicates some NES-type character is present.

The invention claimed is:

1. A microcrystalline zeolite represented by the empirical formula:

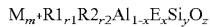

$$M_{m'}R1_{r1}R2_{r2}Al_{1-x}E_xSi_yO_z$$

where M represents sodium or a combination of sodium and potassium exchangeable cations, "m" is the mole ratio of M to (Al+E) and varies from about 0.05 to about 5, R1 is a singly charged propyltrimethylammonium cation, "r1" is the mole ratio of R1 to (Al+E) and has a value of about 0.25 to about 8.0, R2 is an amine, "r2" is the mole ratio of R2 to (Al+E) and has a value of about 0.0 to about 5, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation: z=(m+r1+r2+3+4·y)/2 wherein said microcrystalline zeolite has an EUO-NES-NON framework structure comprising from about 33-34 wt-% EUO, 24-31 wt-% NES and 34-43 wt-% NON.

2. The microcrystalline zeolite of claim 1 wherein said microcrystalline zeolite is characterized in that it has the x-ray diffraction pattern having at least the d-spacing's and intensities set forth in Table A

TABLE A

| 2θ | d(Å) | I/I$_0$ % |
|---|---|---|
| 7.96-8.06 | 10.96-11.09 | m |
| 8.72-8.85 | 9.97-10.10 | w |
| 9.40-9.41 | 9.36-9.40 | w |
| 12.96-13.01 | 6.79-6.82 | w |
| 19.10-19.17 | 4.62-4.64 | m |
| 20.54-20.62 | 4.30-4.32 | vs |
| 22.23-22.33 | 3.97-3.99 | m |
| 23.29-23.42 | 3.79-3.81 | m-w |
| 23.97-24.08 | 3.69-3.70 | m |
| 26.01-26.13 | 3.40-3.42 | w |
| 26.54-26.62 | 3.34-3.35 | m |
| 27.24-27.32 | 3.26-3.27 | m |
| 28.86-29.00 | 3.07-3.09 | w |
| 33.16-33.29 | 2.68-2.69 | w |
| 35.46-35.52 | 2.52 | w. |

3. A microcrystalline zeolite represented by the empirical formula:

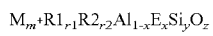

where M represents sodium or a combination of sodium and potassium exchangeable cations, "m" is the mole ratio of M to (Al+E) and varies from about 0.05 to about 5, R1 is a singly charged propyltrimethylammonium cation, "r1" is the mole ratio of R1 to (Al+E) and has a value of about 0.25 to about 8.0, R2 is an amine, "r2" is the mole ratio of R2 to (Al+E) and has a value of about 0.0 to about 5, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation: z=(m+r1+r2+3+4·y)/2 wherein said microcrystalline zeolite is calcined and is characterized in that it has the x-ray diffraction pattern having at least the d-spacings and intensities set forth in Table B:

TABLE B

| 2θ | d(Å) | I/I₀ % |
|---|---|---|
| 7.99-8.00 | 11.04 | s |
| 8.74 | 10.11 | w |
| 9.42 | 9.38 | m |
| 12.96-12.99 | 6.80-6.82 | w |
| 15.24-15.27 | 5.79-5.80 | w |
| 15.98 | 5.54 | w |
| 19.22-19.26 | 4.60-4.61 | m |
| 20.56-20.62 | 4.30-4.31 | vs |
| 22.28-22.32 | 3.97-3.98 | s |
| 23.30 | 3.81 | m |
| 23.98-24.00 | 3.69-3.70 | m |
| 26.05-26.06 | 3.41 | w |
| 26.67-26.72 | 3.33 | m |
| 27.30-27.35 | 3.25-3.26 | s |
| 28.94-29.01 | 3.07-3.08 | w |
| 33.24-33.29 | 2.68-2.69 | w |
| 35.66-35.68 | 2.51 | w. |

4. The microcrystalline zeolite of claim 3 wherein said microcrystalline zeolite has a Si/Al ratio of about 10 to 25.

5. The microcrystalline zeolite of claim 3 further comprising alumina.

6. The microcrystalline zeolite of claim 5 comprising about 30 wt-% of said alumina.

7. A process for preparing a microporous crystalline zeolite having a three-dimensional framework of at least AlO₂ and SiO₂ tetrahedral units and an empirical composition in the as synthesized and anhydrous basis expressed by an empirical formula of: represented by the empirical formula:

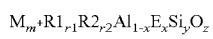

where M represents sodium or a combination of sodium and potassium exchangeable cations, "m" is the mole ratio of M to (Al+E) and varies from about 0.05 to about 3.5, R1 is a singly charged propyltrimethylammonium cation, "r1" is the mole ratio of R1 to (Al+E) and has a value of about 0.25 to about 8.0, R2 is an amine, "r2" is the mole ratio of R2 to (Al+E) and has a value of about 0.0 to about 5, E is an element selected from the group consisting of gallium, iron, boron and mixtures thereof, "x" is the mole fraction of E and has a value from 0 to about 1.0, "y" is the mole ratio of Si to (Al+E) and varies from greater than 5 to about 40 and "z" is the mole ratio of O to (Al+E) and has a value determined by the equation: z=(m+r1+r2+3+4·y)/2 and is characterized in that it has the x-ray diffraction pattern having at least the d-spacings and intensities set forth in Table A:

TABLE A

| 2θ | d(Å) | I/I₀ % |
|---|---|---|
| 7.96-8.06 | 10.96-11.09 | m |
| 8.72-8.85 | 9.97-10.10 | w |
| 9.40-9.41 | 9.36-9.40 | w |
| 12.96-13.01 | 6.79-6.82 | w |
| 19.10-19.17 | 4.62-4.64 | m |
| 20.54-20.62 | 4.30-4.32 | vs |
| 22.23-22.33 | 3.97-3.99 | m |
| 23.29-23.42 | 3.79-3.81 | m-w |
| 23.97-24.08 | 3.69-3.70 | m |
| 26.01-26.13 | 3.40-3.42 | w |
| 26.54-26.62 | 3.34-3.35 | m |
| 27.24-27.32 | 3.26-3.27 | m |
| 28.86-29.00 | 3.07-3.09 | w |
| 33.16-33.29 | 2.68-2.69 | w |
| 35.46-35.52 | 2.52 | w | and is thermally stable up to a temperature of at least 600° C. and has a BET surface area of less than about 420 m²/g; the process comprising forming a reaction mixture containing reactive sources of M, R, Al, Si and optionally E and heating the reaction mixture at a temperature of about 150° to about 200° C., for a time sufficient to form the zeolite, the reaction mixture having a composition expressed in terms of mole ratios of the oxides of:

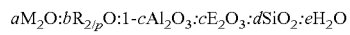

where "a" has a value of about 0.05 to about 1.25, "b" has a value of about 1.5 to about 40, "c" has a value of 0 to about 1.0, "d" has a value of about 4 to about 40, "e" has a value of about 25 to about 4000.

8. The process of claim 7 where the source of M is selected from the group consisting of halide salts, nitrate salts, acetate salts, hydroxides, sulfate salts and mixtures thereof.

9. The process of claim 7 where the source of E is selected from the group consisting of alkali borates, boric acid, precipitated gallium oxyhydroxide, gallium sulfate, ferric sulfate, ferric chloride and mixtures thereof.

10. The process of claim 7 where the aluminum source is selected from the group consisting of aluminum isopropoxide, aluminum sec-butoxide, precipitated alumina, Al(OH)₃, aluminum metal and aluminum salts.

11. The process of claim 7 where the silicon source is selected from the group consisting of tetraethyorthosilicate, fumed silica, colloidal silica and precipitated silica.

12. The process of claim 7 where the reaction mixture is reacted at a temperature of about 150° C. to about 185° C. for a time of about 1 day to about 3 weeks.

13. The process of claim 7 where the reaction mixture is reacted at a temperature of about 165° C. to about 175° C. for a time of about 1 day to about 3 weeks.

14. The process of claim 7 further comprising adding UZM-43 seeds to the reaction mixture.

15. The process of claim 7 wherein the quaternary ammonium organic template source is selected from the group consisting of propyl trimethylammonium hydroxide, propyl trimethylammonium fluoride, propyl trimethylammonium bromide, propyl trimethylammonium chloride, or combinations thereof.

16. The process of claim 7 where R1 is propyl trimethylammonium hydroxide.

17. The process of claim 7 where R1 is only propyl trimethylammonium bromide.

18. The process of claim 7 where R2 is the organic amine template source is selected from the group consisting of morpholine, dimethylcyclohexylamine, piperidine, hexamethylimine, tripropylamine, triethylamine, dipropylamine, propylamine, dimethylamine, diethylamine, or combinations thereof.

19. The process of claim 7 wherein said amine is from an organic amine template source comprising morpholine.

* * * * *